United States Patent
Meller et al.

[11] Patent Number: 5,892,144
[45] Date of Patent: Apr. 6, 1999

[54] BIOSENSOR

[75] Inventors: Paul Meller, Langen; Norbert Madry; Carsten Schelp, both of Marburg; Andrzej Grzegorzewski, Achim, all of Germany

[73] Assignee: Behringwerke Aktiengesellschaft, Marburg, Germany

[21] Appl. No.: 629,262

[22] Filed: Apr. 8, 1996

[30] Foreign Application Priority Data

Apr. 10, 1995 [DE] Germany ............... 195 12 710.2

[51] Int. Cl.⁶ .................................................. G01N 29/00
[52] U.S. Cl. ........................................ 73/64.42; 73/59.25
[58] Field of Search ................. 73/64.42, 54.24, 73/54.25; 422/82.01

[56] References Cited

U.S. PATENT DOCUMENTS

| | | |
|---|---|---|
| 4,236,893 | 12/1980 | Rice . |
| 4,695,956 | 9/1987 | LeVeen et al. .................. 364/416 |
| 4,735,906 | 4/1988 | Bastiaans . |
| 4,849,340 | 7/1989 | Oberhardt ............................ 435/13 |
| 5,211,054 | 5/1993 | Muramatsu et al. ............... 73/64.42 |
| 5,494,639 | 2/1996 | Grzegorzewski .............. 422/82.01 |

FOREIGN PATENT DOCUMENTS

| | | |
|---|---|---|
| 0 177 858 A1 | 4/1986 | European Pat. Off. . |
| 0 295 965 B1 | 12/1988 | European Pat. Off. . |
| 0 177 853 B1 | 3/1990 | European Pat. Off. . |
| 0 408 578 B1 | 1/1991 | European Pat. Off. . |
| 0 453 224 A2 | 10/1991 | European Pat. Off. . |
| 0 494 896 B1 | 7/1994 | European Pat. Off. . |
| WO 89/09937 | 10/1989 | WIPO . |

OTHER PUBLICATIONS

Muramatsu et al., "A Quartz Crystal Viscosity Sensor For Monitoring Coagulation Reaction and its Application to a Multichannel Coagulation Detector", Biosensors & Bioelectronics, 6:353–358 (1991).

Muratsugu et al., "Detection of Antistreptolysin O Antibody: Application of an Initial Rate Method of Latex Piezoelectric Immunoassay", Anal. Chem., 64(21) :2483–2487 (1992).

Shana et al., "Quartz Crystal Resonators as Sensors in Liquids Using the Acoustoelectric Effect", Anal. Chem., 66 (13) :1955–1964 (1994).

*Primary Examiner*—Michael Brock
*Assistant Examiner*—Jay L. Politzer
*Attorney, Agent, or Firm*—Finnegan, Henderson, Farabow, Garrett & Dunner, L.L.P.

[57] ABSTRACT

A biosensor (10) for measuring changes in viscosity, density and/or mass in a fluid to be examined, for example a blood coagulation sensor or immunoassay system. According to the invention, the reagents necessary for the test are contained in a support (13) which is put onto the measurement surface (18) of a piezoelectric element (8). As a blood coagulation sensor, the measurement surface (18) may according to the invention itself have a coagulation activator action or else be coated with coagulation activators.

22 Claims, 1 Drawing Sheet

BIOSENSOR

The invention relates to a biosensor having a piezoelectric element as resonant circuit, a measurement surface of which is exposed to components of a fluid to be examined by reaction with reagents necessary for the test, viscosity and/or density changes in the fluid to be examined and/or mass changes due to deposition on the measurement surface of the piezoelectric element leading to changes in the resonant circuit parameters and being evaluated by a corresponding electronic evaluation circuit.

General comments on quartz crystal resonators are found in the article by Zack A. Shana and Fabien Josse in Anal. Chem. 1994, 66, pages 1955–1964, entitled "Quartz Crystal Resonators as Sensors in Liquids Using the Acoustoelectric Effect".

EP-A-0,177,858 describes an arrangement with a biosensor, with which it is intended to measure the coagulation time of blood. A quartz crystal, which is connected as a resonant circuit to an oscillator with fixed frequency, is arranged in a measurement chamber that can be sealed with a lid. Before introduction into the measurement chamber, the blood to be examined is thoroughly mixed with reagents necessary for coagulation, and thereupon introduced into the measurement chamber. The coagulation time is subsequently measured by evaluating a decrease in amplitude at the quartz crystal due to the damping or detuning of the resonant circuit by the coagulating blood. The time elapsing before coagulation is measured using an electronic stopwatch. This known biosensor has the disadvantage that, after a measurement process has been completed, its measurement chamber or the measurement surface of the quartz crystal can only be cleaned with great difficulty and, in addition, it is necessary to pay particular attention to and monitor the time which elapses from mixing the blood with reagents necessary for coagulation until application to the measurement surface, in order to avoid erroneous measurements.

The article "A quartz crystal viscosity sensor for monitoring coagulation reaction and its application to a multichannel coagulation detector" by Muramatsu et al. in Biosensors & Bioelectronics 6 (1991) pages 353–358 describes a device for determining blood coagulation, in which it is necessary to mix the test-specific components, preincubate them at a predetermined temperature and apply this mixture to the mass-sensitive test face of the quartz crystal. A disadvantage in the case of this method is that the influences of manual handling can lead to inaccuracies.

Biosensors for detecting antigen-antibody reactions, which operate using piezoelectric elements, for example a quartz crystal, are also described. In the case of such biosensors an antigen-antibody is applied on the measurement surface of the piezoelectric element, and the piezoelectric element is subsequently immersed the fluid to be examined, in order to measure and evaluate the detuning which then takes place of the piezoelectric element as resonant circuit. Such biosensors are described, for example, in U.S. Pat. Nos. 4,236,893 and 4,735,906. However, these described biosensors having an immunocomponent on the measurement surface have the disadvantage that the measurement surface of the piezoelectric element or quartz is already modified by the coating, so that it is no longer possible to measure the frequency of oscillation of the piezoelectric element in the unloaded state, which is highly disadvantageous in measurements where the piezoelectric element is used as mass-sensitive element.

This group of biosensors, in which application of biological components is employed, also includes the following:

EP-A-0,494,896 describes immunoassays using modified quartz crystal microbalances having piezoelectric crystals. These are modified by applying biological components on the crystal surface or on a polymer intermediate layer. Detection takes place by means of an enzymatic amplification mechanism which produces a product that causes a change in mass on the crystal surface due to adsorption or due to a reaction with the polymer intermediate layer. EP-A-0,408,578 describes immunoassays in which an analyte fixing reagent is bound on a substrate surface that is fixed by means of a spacer above the mass-sensitive face. Detection then takes place as described in EP-A-0,494,896. EP-A-0,295,965 describes immunoassay methods in which particle-enhanced tests are carried out. The particle-enhanced immunocomplexes are compacted on a modified sensor surface, on which binding partners have been immobilized, after an immunoreaction by drying or application of a magnetic field, in the case of magnetic particles, on the sensor surface.

The article "Detection of Antistreptolysin O Antibody: Application of an Initial Rate Method of Latex Piezoelectric Immunoassay" by Muratsugu et al. in Anal. Chem. 1992, 46, pages 2483–2487 describes a method termed "Latex piezoelectric immunoassay" wherein, instead of the otherwise customary visual detection of the latex agglutination by means of turbidimetric and nephelometric methods, use is made of a piezoelectric crystal which detects the viscosity or density change in the reaction solution.

The arrangements referred to have the disadvantage that the required sensitivities and detection limits can be achieved only by modifications of the sensor surface and amplification mechanisms. In addition, operation is complex and elaborate. Application for immunoassays requires many manual operations which may lead to inaccuracies. Particularly for the piezoelectric structures used in coagulation diagnostics, the very complex manual operations (mixing the reagents and pre-incubation, application of the sample) lead to inaccuracies in the determination of the coagulation time of the sample.

The object of the present invention is to obtain a biosensor having a piezoelectric element as resonant circuit, which permits viscosity and/or density changes in a fluid to be examined and/or mass changes due to deposition on the piezoelectric element, which is of simple design, which does not require complex procedural steps during operation and does not make prior mixing of the reaction components with the sample to be measured necessary, and which leads to an increased measurement accuracy.

This object is achieved according to the present invention with a biosensor according to the preamble of claim 1, in that the biosensor is equipped with a coagulation-initiating surface, a) it being possible for this surface to be a support which contains the reagents necessary for the test,
b) a coagulation-initiating coating, or
c) for the support per se to be the surface as such; and
d) the fluid to be examined can be applied onto the support and comes into contact with the reagents and the measurement surface.

In an advantageous embodiment of the biosensor according to the invention, the support is provided with a filter layer, for the separation of substances that interfere with the test, on the side remote from the measurement surface, or the support is provided with a sample-conditioning layer on the side remote from the measuring surface. As a result, any interfering suspended matter in the fluids to be examined can be retained or the fluid can be conditioned for the test, for example the pH value can be adjusted.

A variant provides that either the sensor surface is used as coagulation activator without additional coating or the support itself, without containing coagulation activator reagents, already has a coagulation activation action, and that the fluid to be examined can be applied onto the support and comes into contact with the agents and the measurement surface.

Further advantageous embodiments are described in the claims.

A biosensor is thereby obtained with which so-called "dry tests" can be carried out, i.e. the fluid to be examined can be introduced into the biosensor for the test without additional reagents being required, since all reagent components or agents are already contained in the biosensor. These reagents necessary for the test, already present in the biosensor, also do not load the measurement surface of the piezoelectric element, so that accurate measurements or tests are possible.

The biosensor according to the invention is preferably designed as a single-use article, which is possible and economical because of the simple structure and the concomitant low costs. Preferably, the biosensor can be used for determining parameters of the blood coagulation system; it can, however, also be used to great advantage for immunoassay.

When coagulation activator supports are used, the material advantageously consists of glass balls, glass particles, glass dust, glass fibers, nonwoven glass materials or similar particulate systems which are applied directly on the sensor surface or in the measurement space in the form of a thin film or in loose form. Use may also be made of other coagulation activator substances known per se to the person skilled in the art such as, for example, kaolins, feldspars, silicates or other activator substances which have a negative surface charge. In the case of such a solution it is not detrimental for the substances to rest on the measurement surface of the piezoelectric element; surprisingly, this contact does not lead to a nominal preloading of the piezoelectric element, so that the oscillation parameters can still be measured with full accuracy before filling with the fluid to be examined.

When the support is used for the reagents necessary for the test, the support preferably consists of nonwoven material or paper; another advantageous solution also consists in the support consisting of a synthetic woven or knitted fabric.

In a further advantageous embodiment of the biosensor according to the invention, the coagulation activators are provided with a filter layer, for the separation of substances that interfere with the test, on the side remote from the measurement surface or the support is provided with a sample-conditioning layer on the side remote from the measuring surface. As a result, any interfering suspended materials in the fluid to be examined can be retained or the fluid can be conditioned for the test, for example the pH value can be adjusted.

If the biosensor according to the invention is used as a blood coagulation sensor, then the support contains coagulation-initiating reagents or the piezoelectric element is itself used as a coagulation initiator. A further variant of the biosensor according to the invention as a blood coagulation sensor provides that, instead of a support that carries reagents, a coagulation-initiating substance is put onto or applied onto the piezoelectric element.

In the case of immunoassay use, the support contains immunocomponents as reagents. The immunocomponents are advantageously bound to particles which are known per se to the person skilled in the art from nephelometric or turbidimetric methods. These particles can, in similar fashion to the coagulation activators, also be put directly onto the measurement surface or applied in a readily water-soluble film in the measurement chamber.

In a preferred measurement arrangement with a biosensor according to the invention, an oscillator circuit and a microprocessor circuit as electronic evaluation circuit are provided, the piezoelectric element is inserted as frequency-determining element into the oscillator circuit and the frequency changes are digitally measured by the microprocessor circuit and evaluated. In such a case, the microprocessor circuit can take the time component into account in the measurement and, by means of corresponding programming, carry out a qualitative and/or quantitative assessment. In order to obtain particularly stable measurements, the biosensor is preferably provided with a temperature-control device for keeping its temperature at a constant value. With a measurement arrangement with a microprocessor circuit it is possible to employ the temperature dependence of the piezoelectric element to measure the temperature in the biosensor in order, as a function thereof, to control the evaluation or to carry out thermal regulation of the biosensor to a constant temperature.

Further advantageous developments of the invention can be found in the subclaims.

The invention is explained in more detail below with the aid of exemplary embodiments with reference to the appended drawings, in which.

Figure 1:
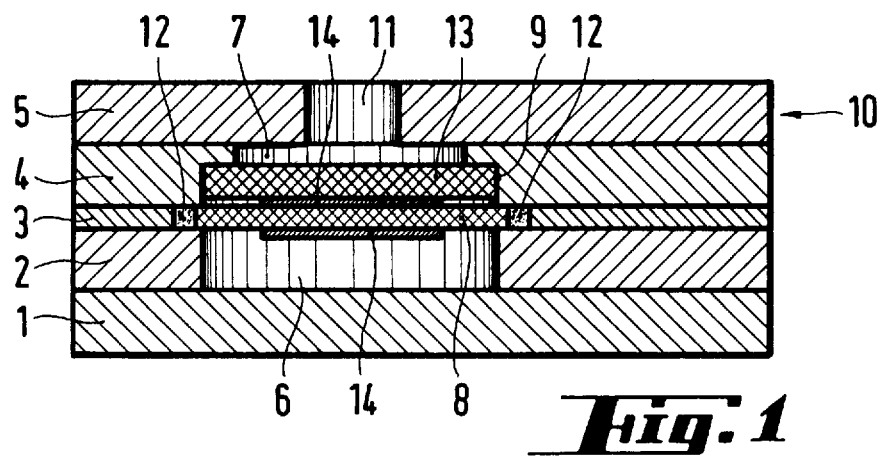
FIG. 1 shows a cross section through a biosensor according to the invention in sandwich construction.

The biosensor with sandwich construction as shown in FIG. 1 contains five layers. A first layer 1 forms the bottom of the biosensor 2, a second layer 2 forms a free space 6 below a piezoelectric element 8, by means of a corresponding recess, a third layer 3 serves as support for the piezoelectric element 8, a fourth layer forms a measurement chamber 7 above the piezoelectric element 8, by means of a corresponding recess 9, and, finally, a fifth layer 8 forms a seal for the measurement chamber 7 above the piezoelectric element 8, an access hole 11 in the form of a bore permitting the measurement chamber 7 to be filled with the fluid to be examined. It is also possible to provide a membrane that is permeable to the fluid to be examined instead of the covering layer 5 with a bore 11.

Figure 2:
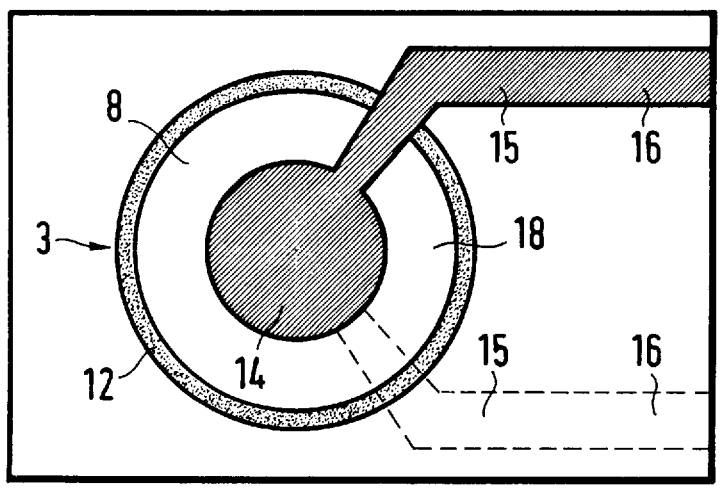
FIG. 2 shows a plan view of a layer, supporting the piezoelectric element, of the biosensor according to FIG. 1.

As can be seen from FIG. 2, the piezoelectric element is arranged on a support plate forming the third layer 3, specifically the piezoelectric element 8 is bonded into a corresponding recess in the third layer 3 by means of an adhesive 12. Both faces of the piezoelectric element 8 are provided with electrodes 14 which are connected to terminal faces 16 via conductor tracks 15 applied onto the third layer 3. The upper face (visible in FIG. 1), given the reference number 18 in FIG. 2, forms the measurement surface of the piezoelectric element 8, the face of the electrodes 14 being intended to be taken as the density-sensitive or viscosity-sensitive or mass-sensitive face.

A support 13 which rests loosely on the measurement surface 18 of the piezoelectric element 8 is fitted into the measurement chamber 7 (see FIG. 1) of the biosensor 10, i.e. into the recess 9. The support 13 is used for holding reagents necessary for the test, with which the fluid to be examined is intended to react. During introduction of the fluid to be examined via the access hole or the bore 11, the fluid reacts with the reagents situated in the support 13 and, together with the reagents, reaches the measurement surface 18 of the piezoelectric element 8. This thus means that the start of the measurement is exactly established by introduction of the fluid to be examined, and the speed with which the fluid to be examined is mixed with the reagents and then introduced to the biosensor does not, as previously, depend on the skill of the operator.

The biosensor 10 in sandwich form, represented in FIGS. 1 and 2, can be produced in suitable fashion, for example by bonding together the individual layers 1–5. The individual layers 1–5 preferably consist of synthetic films; but the use of paper for some of the layers is also possible. It is further possible to combine some of the layers 1–5, for example layers 1 and 2 as well as 4 and 5, the respective recesses for the free space 6 and the measurement chamber 7 being produced as an impression.

The biosensor 10 is very simple and inexpensive to produce, so that it can be designed and used as a single-use biosensor. The single-use form has, primarily, the advantage that the biosensor 10 can be delivered ready for use and provided with the reagents necessary for the test; reuse would not be expedient with such a design.

Figure 3:
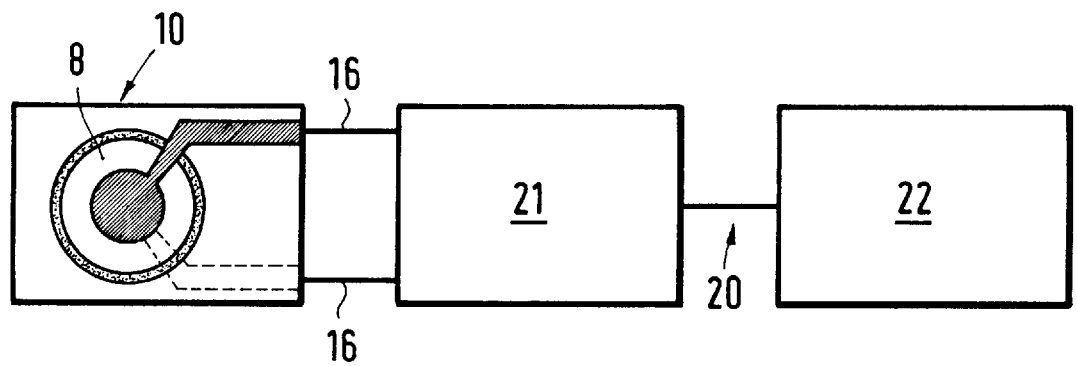
FIG. 3 shows a block diagram of a measurement arrangement with the biosensor according to the invention.

The measurement arrangement shown in FIG. 3 contains an evaluation circuit 20 which has an oscillator circuit 21, a microprocessor circuit 22 as well as the biosensor 10, the piezoelectric element 8 of which is connected to the oscillator circuit 21 via the terminal faces 16. The oscillator circuit 21 uses the piezoelectric element 8, which is expediently a quartz crystal, as frequency-determining element, while the microprocessor circuit 22 has a corresponding frequency-measurement arrangement for measuring the frequency of oscillation of the oscillator 21. The microprocessor can further be programmed and designed in such a way that it evaluates the frequency changes or other parameters of the piezoelectric element 8 or of the oscillator circuit 21 while taking into account the time component of the corresponding changes. By virtue of corresponding programming, a suitable evaluation can be carried out on the basis of these measured values and can be output on a display or another output unit (not represented).

Since the oscillation parameters, in particular the frequency of oscillation, of the piezoelectric element 8 are temperature dependent, it is expedient to keep the temperature of the piezoelectric element at a constant value. For this purpose, a suitable temperature control circuit for the piezoelectric element is provided, the temperature dependence of the piezoelectric element 8 being advantageously used for measuring the actual temperature. By virtue of a suitable control circuit, which is expediently constructed with the microprocessor that is present, suitable temperature control can then be produced, which keeps the operating parameters of the piezoelectric element constant in the intervals between tests. Such a control circuit is not shown in detail.

Some examples in conjunction with experiments will now be explained below.

Exemplary embodiment with reference to the determination of the coagulation times (prothrombin time) of lyophilized normal human plasma pool and lyophilized controls Preimpregnation: a paper from the company Macherey and Nagel (MN 215) which is immersed in a 0.5% gelatin solution is used as support material for the support 13. Excess liquid is removed by rolling off through two metal rollers, and the paper is subsequently dried for 60 minutes at 50° C. 0.1M calcium chloride solution is applied according to the same procedure. Drying is then carried out for 30 minutes, again at 50° C.

Application of the coagulation reagents: 100 µl phospholipon 25 P (100 g/l, Natterman) and 100 µl tissue factor (1 g/l, Behringwerke AG) are mixed with 25 µl 20% Triton X 100 and incubated for 2 hours at −20° C. This solution is diluted at 1:5 with an impregnation buffer (0.1% HSA, 0.1% Haemaccel, 0.1% Thiocid in 20 mM Hepes pH 7.3) and applied onto the paper, preferably by soaking. Drying is then carried out within 20 minutes at 37° C.

Determination of the coagulation time of a plasma sample (prothrombin time) (Quick's test):

The paper prepared in this way is cut to a suitable surface area and put directly onto the measurement surface 18 of the piezoelectric element 8. The piezoelectric element 8 is connected to a suitable electronic circuit for excitation and measurement of the natural frequency of oscillation. The frequency of oscillation is acquired, for example with a frequency counter of the company Keithley (Model 775) with a data link to a data acquisition PC.

In order to determine the coagulation time using Quick's test, Standard Human Plasma (Ch.-B. 502 546, Behringwerke AG), Pathoplasma I (Ch.-B. 502 876, Behringwerke AG) and II (Ch.-B. 502 969, Behringwerke AG) were used. The sample (20 µl) is applied to the support 13 and the decrease in the frequency of oscillation over time is monitored. The coagulation system of the plasma sample is activated by thromboplastin and calcium ions. After a delay phase, initiation of the coagulation becomes observable through a decrease in the frequency of oscillation of the piezoelectric element 8 towards low values. With the aid of the typical curve profile recognized evaluation methods can be used to determine the coagulation time of the samples.

During the series of measurements, different coagulation times were established for the plasma samples used. The measurement results are represented in the following table:

Determination of the prothrombin time of the Pathoplasma I sample with the biosensor 10 in comparison with the specified set-point values for Standard Human Plasma and Pathoplasma II. (The average values of two determinations are specified.)

TABLE 1

|  |  | Standard Human Plasma | Pathoplasma II | Sample: Pathoplasma I |
|---|---|---|---|---|
| Set-point values | % of standard | 98 | 13 | 24.3 |
|  | Interval |  | 10–16 | 21.3–27.3 |
| Sensor calibration | % of standard | 98 | 13 |  |
| Value found | % of standard |  |  | 23.6 |

Exemplary embodiment with reference to the determination of whole blood

A nonwoven glass fiber mat from the company Whatman (GFF) was used as coagulation activator for the support.

Determination of the coagulation time of whole blood (recalcified citrated whole blood):

The nonwoven mat is cut to a suitable surface area and applied directly onto the measurement surface 18 of the piezoelectric element 8. The piezoelectric element 8 is connected to a suitable electronic circuit for excitation and measurement of the natural frequency of oscillation. The frequency of oscillation is acquired, for example with a frequency counter of the company Keithley (Model 775) with a data link to a data acquisition PC.

80 µl of whole blood are pipetted into the measurement chamber and the decrease in the frequency of oscillation over time is monitored. The coagulation system of the sample is activated by the coagulation activator surface of the nonwoven mat. After a delay phase, the incipient coagulation cascade becomes observable through a decrease in the frequency of oscillation of the piezoelectric element 8 toward low values. With the aid of the typical curve profile recognized evaluation methods can be used to determine the coagulation time of the samples.

Exemplary embodiment relating to the determination of the coagulation time of whole blood.

The piezoelectric element 8 is connected to a suitable electronic circuit for excitation and measurement of the natural frequency of oscillation. The frequency of oscillation is acquired, for example with a frequency counter of the company Keithley (Model 775) with a data link to a data acquisition PC.

80 µl of whole blood (recalcified citrated whole blood) are pipetted into the measurement chamber which does not contain any coagulation activator substances or a support material, and the decrease in the frequency of oscillation over time is monitored. The coagulation system of the sample is activated by the coagulation activator surface of the sensor. After a delay phase, the incipient coagulation cascade becomes observable through a decrease in the frequency of oscillation of the piezoelectric element 8 toward low values. With the aid of the typical curve profile recognized evaluation methods can be used to determine the coagulation time of the samples.

Exemplary embodiment of a latex-enhanced immunoassay for determining rheumatoid factors (Rf test)

The preimpregnated support materials are impregnated with Rf latex reagents, as described in the first example, and used in the same structure. When a Rf-positive sample is added, the agglutination reaction takes place, which is monitored by the decrease in the frequency of oscillation of the piezoelectric element 8. The Rf content is then determined either by determining the end point or by means of the reaction rate, which is connected with the change in frequency as a function of time.

We claim:

1. A biosensor comprising:
    a piezoelectric element for providing an output signal in response to oscillation, the piezoelectric element having a measurement surface for exposure to a fluid to be examined and test reagents for reacting with the fluid, viscosity and/or density changes in the fluid to be examined and/or mass changes due to deposition on the measurement surface of the piezoelectric element causing changes in the output signal of the piezoelectric element so that the output signal may be evaluated by a corresponding electronic evaluation circuit; and
    a support having a coagulation-initiating surface, different from the measuring surface, the support being in contact with the measurement surface of the piezoelectric element so that the fluid to be examined can be applied to the support and, if appropriate, contact the reagents and the measurement surface.

2. The biosensor as claimed in claim 1, wherein the measurement surface lacks a coagulation activator coating.

3. The biosensor as claimed in claim 1, wherein the support provides coagulation activation action without coagulation activator reagents.

4. The biosensor as claimed in claim 1, wherein the piezoelectric element (8) is a quartz crystal designed as a shear-mode oscillator.

5. The biosensor as claimed in claim 1, comprising a membrane covering a measurement chamber (7), the membrane being permeable to fluid.

6. The biosensor as claimed in claim 1, wherein the support contains the test reagents.

7. The biosensor as claimed in claim 6, wherein the support (13) consists of nonwoven material or paper.

8. The biosensor as claimed in claim 6, wherein the support (13) consists of a synthetic woven or knitted fabric.

9. The biosensor as claimed in claim 6, wherein the support (13) consists of glass spheres, glass fibers, glass particles or glass dust.

10. The biosensor as claimed in claim 6, wherein the support (13) consists of kaolin, feldspars or silicate.

11. The biosensor as claimed in claim 6, wherein the support (13) consists of a substrate having a negative surface charge.

12. The biosensor as claimed in claim 3, wherein the support (13) is provided with a filter layer for separating a substance that interferes with the test, the filter layer being disposed on a side of the bisosensor remote from the measurement surface (18).

13. The biosensor as claimed in claim 6, wherein the support (13) is provided with a sample-conditioning layer on a side of the biosensor remote from the measurement surface.

14. The biosensor as claimed in claim 6, wherein the biosensor is a blood coagulation sensor and the support (13) contains coagulation-initiating reagents.

15. The biosensor as claimed in claim 6, wherein the biosensor is for immunoassay use and the support (13) contains immunocomponents as reagents.

16. The biosensor as claimed in claim 1, wherein the biosensor is designed as a single-use article.

17. The biosensor as claimed in claim 16, further comprising a housing having a plurality of layers bonded together in sandwich fashion.

18. The biosensor as claimed in claim 17, wherein the layers of the housing include a first layer forming a closed base, a second layer forming a free space below the piezoelectric element, a third layer holding the piezoelectric element, a fourth layer forming a measurement chamber above the piezoelectric element and holding the support, and a fifth layer forming a lid for the measurement chamber above the piezoelectric element, the fifth layer having an access hole for filling the measurement chamber with the fluid to be examined.

19. The biosensor as claimed in claim 18, wherein the access hole for introducing the fluid to be examined is a bore (11) communicating with the measurement chamber (7).

20. A measurement arrangement comprising:
    a biosensor as claimed in claim 1;
    an oscillator circuit; and
    a microprocessor circuit, the oscillator circuit and the microprocessor circuit forming an electronic evaluation circuit for determining frequency of the output signal from the piezoelectric element, measuring changes of the frequency, and evaluating changes of the frequency.

21. The measurement arrangement as claimed in claim 20, comprising a temperature-control device for keeping temperature of the biosensor at a constant value.

22. The measurement arrangement as claimed in claim 20, wherein the temperature dependence of the piezoelectric element (8) is used to measure the temperature.

* * * * *